United States Patent
Fukushima et al.

(10) Patent No.: US 9,309,307 B2
(45) Date of Patent: Apr. 12, 2016

(54) ANTIBODY AGAINST AMYLOID PRECURSOR PROTEIN SIGNAL PEPTIDE

(75) Inventors: Hitoshi Fukushima, Suwa (JP); Masato Hanamura, Suwa (JP); Mikio Niwa, Tsukuba (JP); Masaji Okamoto, Tsukuba (JP); Tomoko Naoe, Tsukuba (JP); Tetsuhiko Yoshida, Tsukuba (JP)

(73) Assignees: SEIKO EPSON CORPORATION, Tokyo (JP); TOAGOSEI CO., LTD., Tokyo (JP)

( * ) Notice: Subject to any disclaimer, the term of this patent is extended or adjusted under 35 U.S.C. 154(b) by 227 days.

(21) Appl. No.: 13/978,584

(22) PCT Filed: Jan. 6, 2012

(86) PCT No.: PCT/JP2012/050210
§ 371 (c)(1),
(2), (4) Date: Sep. 5, 2013

(87) PCT Pub. No.: WO2012/093732
PCT Pub. Date: Jul. 12, 2012

(65) Prior Publication Data
US 2013/0345408 A1 Dec. 26, 2013

(30) Foreign Application Priority Data

Jan. 7, 2011 (JP) .................................. 2011-002464
Jan. 7, 2011 (JP) .................................. 2011-002465

(51) Int. Cl.
*C12N 5/12* (2006.01)
*C07K 16/18* (2006.01)

(52) U.S. Cl.
CPC .. *C07K 16/18* (2013.01); *C12N 5/12* (2013.01)

(58) Field of Classification Search
CPC .................. A61K 2300/00; A61K 47/48215; A61K 39/00; A61K 2039/55505; A61K 39/385; A61K 39/0007; A61K 38/1716; C07K 16/18
See application file for complete search history.

(56) References Cited

U.S. PATENT DOCUMENTS

| 5,242,932 | A * | 9/1993 | Gandy et al. .................. 514/313 |
| 6,037,521 | A * | 3/2000 | Sato et al. ....................... 800/18 |
| 2010/0209490 | A1 | 8/2010 | Morita et al. |
| 2011/0229912 | A1* | 9/2011 | Cai et al. ........................ 435/7.9 |
| 2011/0269942 | A1 | 11/2011 | Morita et al. |

FOREIGN PATENT DOCUMENTS

| JP | A-2007-517057 | 6/2007 |
| JP | A-2011-16763 | 1/2011 |
| WO | WO 2009/020093 A1 | 2/2009 |
| WO | WO 2009/020094 A1 | 2/2009 |
| WO | 2009/047002 A2 | 4/2009 |
| WO | 2009/053696 A1 | 4/2009 |
| WO | WO 2010/117079 A1 | 10/2010 |

OTHER PUBLICATIONS

Rohn TT et al. (2000) A monoclonal antibody to amyloid precursor protein induces neuronal apoptosis. J. Neurochem. 74:2331-2342.*
Martoglio et al., "Signal Sequences: More than Just Greasy Peptides," *trends in Cell Biology*, Oct. 1998, vol. 8, pp. 410-415.
Henderson et al., "HLA-A2.1-Associated Peptides from a Mutant Cell Line: A Second Pathway of Antigen Presentation," *Science*, 1992, vol. 255, pp. 1264-1266.
Hage et al., "Preprocalcitonin Signal Peptide Generates a Cytotoxic T Lymphocyte-Defined Tumor Epitope Processed by a Proteasome-Independent Pathway," *PNAS*, Jul. 2008, vol. 105, No. 29, pp. 10119-10124.
Abbott, "The Plaque Plan," *Nature*, Nov. 2008, vol. 456, pp. 161-164.
Nikolaev et al., "APP Binds DR6 to Trigger Axon Pruning and Neuron Death via Distinct Caspases," *Nature*, Feb. 2009, vol. 457, pp. 981-989.
International Search Report issued in International Patent Application No. PCT/JP2012/050210 dated Mar. 13, 2012.
International Preliminary Report on Patentability issued in International Patent Application No. PCT/JP2012/050210 dated Jul. 10, 2013.
Harlow et al., *Antibodies; A Laboratory Manual*, Spring Harbor Laboratory, 1988, Chapter 5, pp. 72-77.
Hopp et al., "Prediction of Protein Antigenic Determinants from Amino Acid Sequences," *Proc. Natl. Acad. Sci. USA*, 1981, vol. 78, No. 6, pp. 3824-3828.
Kohler et al., "Continuous Cultures of Fused Cells Secreting Antibody of Predefined Specificity," *Nature*, Aug. 7, 1975, vol. 256, pp. 495-497.
Paliga et al., "Human Amyloid Precursor-like Protein 1 cDNA Cloning, Ectopic Expression in COS-7 Cells and Identification of Soluble Forms in the Cerebrospinal Fluid," Eur. J. Biochem., vol. 250, pp. 354-363, 1997.
Lichtenthaler et al., "A Novel Substrate for Analyzing Alzheimer's Disease γ-Secretase," FEBS Letters, vol. 453, pp. 288-292, 1999.

* cited by examiner

*Primary Examiner* — Kimberly A. Ballard
(74) *Attorney, Agent, or Firm* — Oliff PLC

(57) ABSTRACT

An advantage of some aspects of the invention is to provide an antibody against an amyloid precursor protein signal peptide. The invention provides an amyloid precursor protein signal peptide.

1 Claim, 3 Drawing Sheets

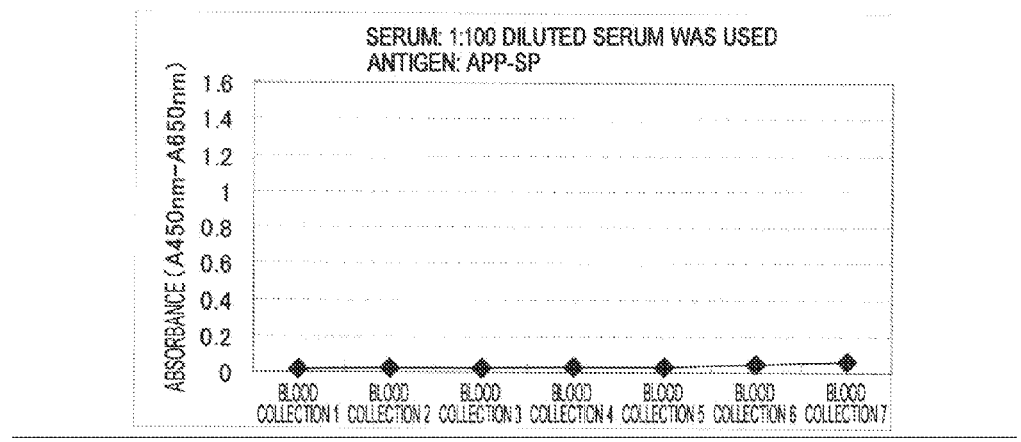

ANTIBODY AGAINST AMYLOID PRECURSOR PROTEIN SIGNAL PEPTIDE

CROSS REFERENCE TO RELATED APPLICATIONS

The present application is based on Japanese Patent Application No. 2001-2464 filed Jan. 7, 2011 and Japanese Patent Application No. 2011-2465 filed Jan. 7, 2011, the contents of which are incorporated herein by reference.

BACKGROUND

1. Technical Field

The present invention relates to an antibody against an amyloid precursor protein signal peptide. The invention also relates to a monoclonal antibody against the amyloid precursor protein signal peptide and a hybridoma producing the same.

2. Related Art

Peptides per se are widely and generally known to have various functions, such as hormone and neurotransmitter, in vivo. Among such peptides, peptides playing a plurality of physiological roles have been reported in recent years. Previously, a short peptide region called a signal peptide had been considered to be only responsible for translocating a newly synthesized protein to the endoplasmic reticulum. However, other physiological roles have been reported one after another in recent years (Trends in Cell Biology, 1998, vol. 8, pp. 410-415).

For example, a portion of the calreticulin signal peptide has been demonstrated to be presented on the cell surface by major histocompatibility complex (MHC) (Science, 1992, vol. 255, pp. 1264-1266). The physiological significance of such phenomenon is considered to be probably a part of a mechanism for monitoring the expression level of the intracellular protein or the production proportion of the normal signal peptide. However, no conclusion has been reached.

It has also been shown that a portion of the calcitonin signal peptide is presented on the surface of non-small cell lung cancer cells by MHC and cytotoxic T cells recognize the signal peptide as an epitope, which has been expected to be useful for the development of a cancer vaccine (Proceedings of the National Academy of Sciences of the United States of America, 2008, vol. 29, no. 105, pp. 10119-10124).

As described above, signal peptides have been each shown to not only be a mere signal guiding a protein to the endoplasmic reticulum but also have a new physiological/pathological significance. Thus, there is no denying that signal peptides that have not been characterized well could be involved as a factor responsible for some kind of important physiological phenomenon, for example, unexplained refractory diseases.

An example of such refractory diseases includes Alzheimer's disease. Alzheimer's disease is advanced dementia having pathological characteristics such as neuronal loss, amyloid β accumulation, and neurofibrillary change in the brain. Based on these pathological characteristics, the hypothesis prevails that amyloid β is a primary cause, and methods for diagnosing/treating Alzheimer's disease have been studied for many years. However, not only a treatment method but also a pathogenic mechanism has not yet been determined. With the foregoing current circumstances in view, the opinion is recently arising that the amyloid β theory may be wrong (Nature, 2008, vol. 456, pp. 161-164). In addition, there is a report suggesting that a factor other than amyloid β is involved in the onset of Alzheimer's disease.

It is disclosed that the region from the N-terminus to the 286th residue of the amyloid precursor protein promotes the degeneration of neurons, and the authors address that it has the possibility of providing a causative substance for Alzheimer's disease other than amyloid β (Nature, 2009, vol. 457, pp. 981-989).

The literature (Nature, 2009, vol. 457, pp. 981-989) discloses that the protein from the N-terminus to the 286th residue of the amyloid precursor protein promotes neuronal degeneration. However, it does not disclose which portion of the region is the essential portion responsible for the neuronal degeneration.

SUMMARY 17 residues from the N-terminal of the amyloid precursor protein include a signal peptide represented by SEQ ID NO: 1 (Met Leu Pro Gly Leu Ala Leu Leu Leu Leu Ala Ala Trp Thr Ala Arg Ala: APP-SP). Thus, APP-SP may contribute to the onset of Alzheimer's disease, and an antibody against the amyloid precursor protein signal peptide (APP-SP) can be expected in future to be useful for use in the diagnosis, treatment, or the like of Alzheimer's disease.

An advantage of some aspects of the invention is to provide the antibody against the amyloid precursor protein signal peptide (APP-SP).

Specifically, some aspects of the invention is as follows:

(1) An antibody against an amyloid precursor protein signal peptide.

(2) The antibody according to item (1), wherein the signal peptide is a peptide having the amino acid sequence of SEQ ID NO: 1.

(3) The antibody according to item (1) or (2), wherein the antibody is obtained using the peptide having the amino acid sequence of SEQ ID NO: 1.

(4) The antibody according to any of items (1) to (3), wherein the antibody is a monoclonal antibody.

(5) A hybridoma producing the monoclonal antibody according to item (4).

(6) A hybridoma indicated by receipt number NITE ABP-1198.

BRIEF DESCRIPTION OF THE DRAWINGS

FIG. 6 shows the results of antibody titer measurement in Reference Example.

DESCRIPTION OF EXEMPLARY EMBODIMENTS

Figure 1:
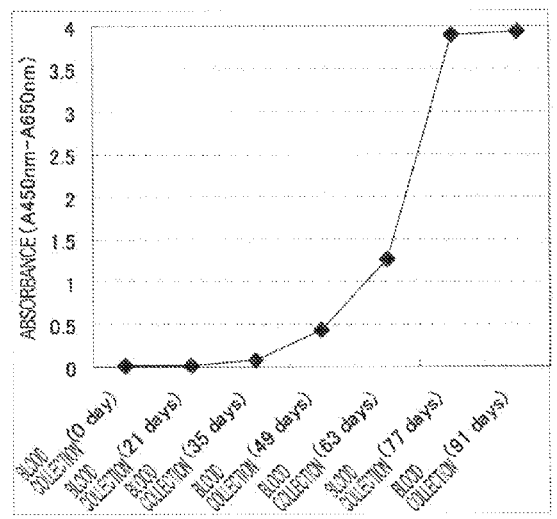
FIG. 1 shows the results of antibody titer measurement in Example 1.

Preferred aspects of the invention will be specifically described below. The invention is not intended to be limited to the following exemplary embodiments, and various modifications can be made within the scope of the gist of the invention.

The antibody according to an aspect of the invention is an antibody against an amyloid precursor protein signal peptide (APP-SP), and the antibody is preferably an antibody specifically recognizing the amyloid precursor protein signal peptide.

According to an aspect of the invention, the term "amyloid precursor protein signal peptide" (or sometimes refereed to as "APP-SP") means (a) a peptide represented by the amino acid sequence described in SEQ ID NO: 1. In the sequence, the description Met (M) means free methionine or S-methylmethionine, and amino acids are represented in one-letter or three-letter code according to IUPAC nomenclature.

The amyloid precursor protein signal peptide may be a naturally-derived isolated peptide or a peptide produced by a heretofore known method. In the field of peptide synthesis, the peptide having the amino acid sequence having SEQ ID NO: 1 is a peptide which can be chemically synthesized by a heretofore known method or can be synthesized by a recombinant technique using a microorganism or the like.

The antibody recognizing APP-SP obtained in an aspect of the invention may be a polyclonal antibody or a monoclonal antibody. Recent research results (see, for example, Nature, 2009, vol. 457, pp. 981-989) have shown that the N-terminal region including a signal peptide portion of amyloid precursor protein promotes the degeneration of neurons. Thus, an antibody which binds to APP-SP receiving attention as a causative substance for Alzheimer's disease as an antigen can be expected in future to be capable of being used for the analysis, diagnosis, treatment, or the like of Alzheimer's disease.

The antibody against APP-SP according to an aspect of the invention is an antibody obtained using an antigen including APP-SP as an antigen, and, for example, as the antigen, (a) a peptide having the amino acid sequence of SEQ ID NO: 1, or (b) a peptide having an amino acid sequence in which one or more amino acids are substituted, deleted, added and/or inserted in the amino acid sequence of SEQ ID NO: 1 may be used.

Preferably as the peptide having the amino acid sequence of SEQ ID NO: 1 is used as an antigen, the obtained antibody recognizes APP-SP.

An antigen-antibody reaction can be performed by using the above-referenced antigen and administering a substance being the antigen to an immunized animal as heretofore known.

The substance being the antigen can be administered to raise an immune response in the immunized animal to produce the antibody against APP-SP according to an aspect of the invention.

Examples of the immunized animal include, but are not limited to, guinea pigs, rats, mice, rabbits, and sheep, which are used as experimental animals.

Examples of method for administering the antigen include, but are not limited to, administration routes such as intraperitoneal, intravenous, intramuscular, and intradermal. Example of administration schedule of the antigen includes, but is not limited to, administering the antigen about 2 to 10 times at 2-week administration intervals to enable the production of the antibody against APP-SP.

In accordance with the administration schedule, a serum sample can be properly collected from the immunized animal to determine the production level of the antibody and confirm whether the immune response is sufficiently raised.

After final immunization, serum can be collected from the immunized animal, followed by purifying it by a heretofore known method to provide the anti APP-SP antibody.

Example of dose of the antigen for priming or booster immunization includes, but is not limited to, a dose of 10 to 200 μg per mouse as dose of an antigen corresponding to APP-SP.

In administering the antigen, an adjuvant may be simultaneously administered. As such adjuvant, a heretofore known adjuvant capable of raising an immune response at a high titer may be used. Examples thereof include Freund's complete adjuvant, Freund's incomplete adjuvant, and aluminum hydroxide.

A method for production of the antibody according to an aspect of the invention can provide a polyclonal antibody, which can be subsequently purified by a heretofore known method to make the antibody highly pure.

Antibody-producing cells can be collected from the spleen or lymph node of the immunized animal producing the antibody to produce a hybridoma and also to provide a monoclonal antibody.

To obtain the antibody against APP-SP according to an aspect of the invention, the following antigen solution can be used.

The antigen solution is a solution containing an antigen for obtaining an antibody against APP-SP. When the antigen is:

(a) a peptide having the amino acid sequence of SEQ ID NO: 1, or (b) a peptide having an amino acid sequence in which one or more amino acids are substituted, deleted, added and/or inserted in the amino acid sequence of SEQ ID NO: 1, a peptide micellar aggregate solution containing the peptide and a PEG surfactant can be used as an antigen solution.

According to an aspect of the invention, the term "PEG surfactant" is not limited, as long as it is a surfactant having a polyethylene glycol (PEG) structure in the molecule.

Examples of the PEG surfactant include a compound in which PEG as a hydrophilic partial structure and a cholesterol skeleton, saturated or unsaturated aliphatic hydrocarbon skeleton having 8 to 20 carbons, or the like as a hydrophobic partial structure are covalently bound through ether bond, ester bond, or the like to the alcoholic hydroxyl group of the terminus of PEG.

The polymerization degree of the repeated structure of the PEG portion (ethylene glycol structure) is, for example, 70 or less and may be 60 or less.

Examples of the PEG surfactant include at least one compound selected from the groups represented by the following formulas.

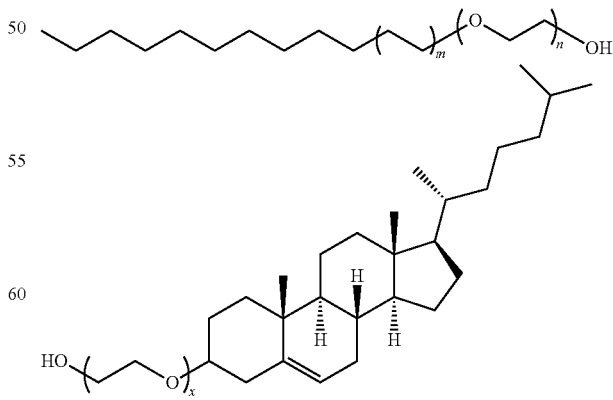

(wherein m is an integer of 0 to 10; n is an integer of 10 to 70; and x is an integer of 30 to 60.)

In the formulas, n and x means the polymerization degrees of the repeated structures.

Examples of the PEG surfactant represented by the at least one compound selected from the groups represented by the above formulas include, in the above-referenced formula, CS-050 in which x is 50, PEG60 in which m is 1 and n is 60, PEG36 in which n is 36, PEG24 in which n is 24, and PEG12 in which n is 12.

Although the mixing of the peptide and a solution containing a PEG surfactant is not limited, the peptide may be mixed in the solution containing a PEG surfactant.

Then, an adjuvant can be mixed with the resultant mixture to make a peptide micellar aggregate solution, followed by administering it to an immunized animal by using the peptide as an antigen to provide an anti APP-SP antibody.

Examples of the adjuvant include Freund's complete adjuvant, Freund's incomplete adjuvant, and aluminum hydroxide.

In mixing the adjuvant, it is preferable to form an emulsion using an ultrasonic processor.

The peptide micellar aggregate solution may be sized to make the particle size distribution of the peptide micellar aggregate uniform. For example, the particle size can be made uniform by a method such as gel filtration chromatography or filtration by a membrane filter.

The particle size of the peptide micellar aggregate may be 5 μm to 200 μm, or may be 5 μm to 100 μm.

The particle size of the peptide micellar aggregate can be measured using a dynamic light scattering particle size measurement apparatus from Nikkiso Co., Ltd.

In an attempt to prepare an antibody against a peptide by a heretofore known method, an antigen is used in which a plurality of molecules of the peptide is covalently bound to a carrier protein.

The binding between the peptide and the carrier protein can be formed by a heretofore known method.

Examples of the carrier protein include keyhole limpet hemocyanin (KLH), bovine serum albumin (BSA), ovalbumin (OVA), mouse serum albumin (MSA), and rabbit serum albumin (RSA).

When the peptide is bound to a carrier protein, cysteine or the like can be added to the N-terminus of the peptide to use a linker binding to the carrier protein.

Such a linker is not limited, as long as it is a linker enabling the covalent binding between the carrier protein and the cysteine-added peptide. However, examples thereof include linkers having functional groups, such as an N-hydroxysuccinimido-activated ester (NHS ester), maleimide, and carbodiimide.

According to an aspect of the invention, in the case of obtaining an antibody against APP-SP by causing a carrier protein to bear an antigen site, the antibody against APP-SP have not been able to be obtained when a peptide having the full-length peptide of APP-SP is used such as (a) a peptide having the amino acid sequence of SEQ ID NO: 1 as an antigen, as disclosed in Examples.

Although the method for administering an antigen to obtain an antibody according to an aspect of the invention is not limited, by measuring the antibody titer, the antigen may be administered until the desired antibody titer is obtained.

The antibody titer can be measured with absorbance. The antibody titer can be measured using a blood sample properly collected from the immunized animal. A blood sample from which foreign substances are removed by centrifugation or the like is preferably used.

The antibody titer can be measured using a heretofore known method, not limited, such as ELISA (enzyme linked immunosorbent assay).

When serum having the desired antibody titer is obtained by the booster immunization, it can be purified by a heretofore known method to provide an anti APP-SP antibody.

For the antibody purification, for example, chromatography purification such as ion-exchange chromatography, gel filtration chromatography, and affinity chromatography, and salting-out or the like can be used. The antibody thus obtained from the blood sample is a polyclonal antibody recognizing APP-SP.

The antigen specificity of the polyclonal antibody can be confirmed by a method such as ELISA.

When the antibody recognizing APP-SP is found to be obtained, antibody-producing cells can be collected from the spleen, lymph node, or the like of the immunized animal by a heretofore known method. The resultant antibody-producing cells can be used for cell fusion to provide hybridoma (fused cells). Antibody-producing cells can be fused with myeloma cells to provide hybridoma.

AS the myeloma cell for fusing with the antibody-producing cell, a commonly available cell line from an animal such as a mouse may be used.

Examples of the myeloma cell include P3-X63-Ag8-U1 and SP2/0-Ag14.

After cell fusion, only hybridoma can be selectively proliferated by screening. As a screening method, cultivation in HAT medium or the like is prefer. At this time, the cultivation may be performed in the presence of feeder cells such as thymus cells to help the proliferation of hybridoma. The antigen specificity of the antibody produced by the resultant hybridoma can be confirmed by measuring the culture supernatant by a known method such as ELISA to select only hybridoma in which desired antibody production has been able to be confirmed. Then, the resultant hybridoma is cloned to remove contaminating undesired cells and thus hybridoma being single clone can be obtained. Examples of cloning method include a limiting dilution method, a soft agar method, and a fibrin gel method. The resultant hybridoma can be freeze preserved by a heretofore known method. A monoclonal antibody can be produced from the cloned hybridoma by a heretofore known method. For example, a monoclonal antibody can be produced by proliferating the hybridoma in the abdominal cavity of a mouse and purifying the ascites fluid containing the monoclonal antibody. A monoclonal antibody can also be produced by culturing the hybridoma in a serum-free medium and purifying the culture supernatant.

The antibody obtained in an aspect of the invention is a mouse antibody when a mouse is used as an immunized animal. The antibody may be made in the form of a chimeric antibody, a humanized antibody, or a human antibody by a heretofore known method. Particularly, a chimeric antibody, humanized antibody, or human antibody recognizing APP-SP is an antibody effective for the treatment of Alzheimer's disease.

EXAMPLES

The invention will be described below in further detail with reference to Examples. However, the invention is not intended to be limited to these Examples.

Example 1

Preparation of Anti APP-SP Monoclonal Antibody (1) Synthesis of Peptide (APP-SP)

The human amyloid precursor protein signal peptide (APP-SP, SEQ ID NO: 1) was chemically synthesized using Fmoc solid phase synthesis method under commission to GL Biochem Ltd. (Shanghai).

The chemically synthesized peptide (APP-SP) was purified by a concentration gradient method in which an ODS column was used and 0.1% trifluoroacetic acid (TFA)-containing water/acetonitrile (MeCN) was used as a mobile phase.

(2) Preparation of Antigen Solution and Immunization Work

By using PEG60 (from Polypure) represented by the following formula (I) as a PEG surfactant, APP-SP chemically synthesized in (1) was adjusted so as to provide 0.8 mg/mL APP-SP and 1% PEG60 to give a mixed aqueous solution in which APP-SP was solubilized.

Formula (I)

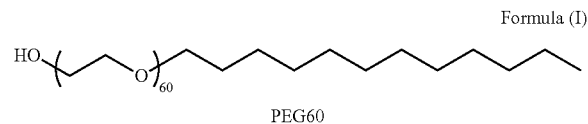

PEG60

The resultant adjusted solution was mixed with an equal volume of an adjuvant, which was then sonicated to give an antigen solution as an emulsion.

The antigen solution was intraperitoneally administered to a female BALB/c mouse according to an administration schedule as shown in Table 1. Blood collection 1 to 7 was performed from the eyeground. As the adjuvant, Freund's complete adjuvant (from Sigma) was used at priming immunization (the 0th day) and Freund's incomplete adjuvant (from Sigma) was used during booster immunization (on or after 14th day).

TABLE 1

| Number of Days | Work Item |
| --- | --- |
| 0 | Blood Collection 1, Antigen Administration (60 μg) |
| 14 | Antigen Administration (60 μg) |
| 21 | Blood Collection 2 |
| 28 | Antigen Administration (60 μg) |
| 35 | Blood Collection 3 |
| 42 | Antigen Administration (60 μg) |
| 49 | Blood Collection 4 |
| 56 | Antigen Administration (60 μg) |
| 63 | Blood Collection 5 |
| 70 | Antigen Administration (60 μg) |
| 77 | Blood Collection 6 |
| 84 | Antigen Administration (60 μg) |
| 91 | Blood Collection 7, Final Antigen Administration (60 μg) |

(3) Measurement of Antibody Titer

To evaluate the results of the immunization performed in (2), ELISA (Enzyme-Linked ImmunoSorbent Assay) was carried out using the serum obtained in the blood collection shown in Table 1, as follows.

APP-SP chemically synthesized in (1) and PEG60 were adjusted to 2.5 mg/mL APP-SP and 1% PEG60, and the resultant adjusted solution was filtered with a 0.45 μm filter. The filtrate was diluted 1:350 with pure water, which was then added in an amount of 100 μL/well to a 96-well microwell plate (from Nunc) and allowed to stand at room temperature overnight. The solution in each well was discarded; thereto was added 250 μL of 3% BSA (from Sigma, Albumin, bovine serum, Fraction V, minimum 96%, lyophilized powder), 0.1% NaN$_3$, and PBS (phosphate buffered saline, pH 7.0) and the resultant was allowed to stand for 3 hours. The solution in each well was discarded; thereto was added 100 μL of each of the sera obtained in blood collection 1 to 7 diluted 1:1,000 with 1% BSA, 0.05% NaN$_3$, and TBS (Tris buffered saline, pH 7.5); and the resultant was allowed to stand for 1 hour. Each well was washed 6 times with PEST (PBS (pH 7.4), 0.1% Tween20); thereto were then added 100 μL of HRP labeled Anti mouse IgG (H+L chain) (from MBL) diluted 1:4,000 with 1% BSA-containing PBS (pH 7.4); and the resultant was allowed to stand for 1 hour. Each well was washed times with PEST; 100 μL of TMB+ (from Dako) was then added thereto; and the resultant was allowed to stand in a dark room for 30 minutes. 100 μL of 2 N sulfuric acid was added thereto, and the resultant was then measured for absorbance at 450 nm and 650 nm. The obtained results are shown in FIG. 1 with the values of absorbance at 450 nm, less that at 650 nm as ordinate.

From the results of FIG. 1, it could be confirmed that an antibody having the property of binding to the human amyloid precursor protein signal peptide (APP-SP) was produced in a mouse body.

(4) Preparation of Hybridoma Producing Anti APP-SP Monoclonal Antibody

Hybridomas were prepared based on B cells of the mouse in which an increase in the antibody titer was observed in (3) Measurement of Antibody Titer under commission to Bex Co., Ltd.

Myeloma cells P3U1 were subjected to cell fusion with B cells prepared by removing the spleen of a mouse at the 94th day after the start of immunization, at which an increase in the titer of the antibody against APP-SP was confirmed, by the action of 50% PEG1500 (from Roche). After fusion, cells were seeded in 10 sheets of 96-well plates to which feeder cells were added in advance, and hybridomas were selectively proliferated in HAT medium.

Cells in the wells in which reactivity was confirmed were subjected to expansion culture in a 24-well plate. After expansion culture, ELISA was performed as in (3), and hybridomas exhibiting positivity were selected and cloned. Cloning was carried out by repeating a limiting dilution method 2 times, and one type of clone producing a monoclonal antibody exhibiting reactivity to APP-SP was finally obtained (hereinafter, this clone is referred to as 12A3 hybridoma). The 12A3 hybridoma was internationally deposited under the Budapest Treaty on the International Recognition of the Deposit of Microorganisms for the Purposes of Patent Procedure in National Institute of Technology and Evaluation, Patent Microorganisms Depositary (NPMD, 2-5-8 Kazusakamatri, Kisarazu-shi, Chiba, Japan), Jan. 6, 2012, and the deposit has been received (receipt number NITE ABP-1198).

(5) Evaluation of Anti APP-SP Monoclonal Antibody Produced by 12A3 Hybridoma

Figure 2:
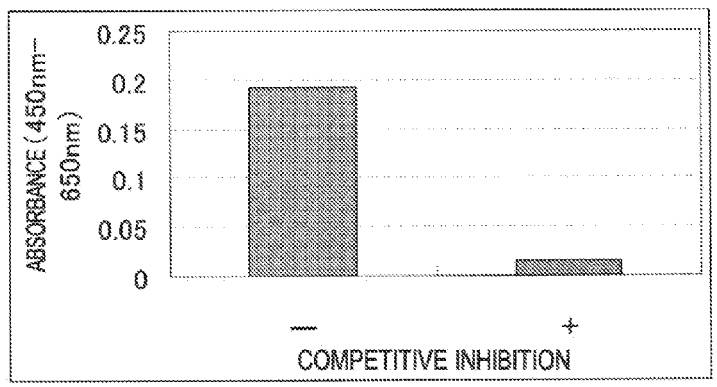
FIG. 2 shows the results of competitive ELISA measurement.

Competitive ELISA was performed to examine the reaction specificity of the anti APP-SP monoclonal antibody for APP-SP. Specifically, in the same way as in (3), for the primary antibody reaction, the supernatant of a culture in which 12A3 hybridoma was cultured was used after 1:3 dilution, and the case of containing 0.2% PEG60 in the solution (competition −) and the case of containing 100 μg/mL APP-SP and 0.2% PEG60 therein (competition +) were prepared and compared. As shown in FIG. 2 for the results, the competition of APP-SP decreased the signal intensity by 92%; thus, the monoclonal antibody could be confirmed to have the property of binding to APP-SP.

When the subclass of the monoclonal antibody produced by 12A3 hybridoma was analyzed using a mouse monoclonal antibody subclass determination kit (from Roche), it was shown to be IgG2a.

(6) Production of Anti APP-SP Monoclonal Antibody

Pristane (from Sigma) was intraperitoneally administered in a volume of 0.5 mL per mouse to 3 female BALB/c mice. After 1 week, $1 \times 10^7$ cells per mouse of 12A3 hybridoma cultured in advance was intraperitoneally administered. After 1 week, ascites fluid was collected and centrifuged to recover the supernatant. From the 3 mice, 9.5 mL of the supernatant was obtained. A saturated ammonium sulfate solution was added dropwise to 50% to the resultant supernatant, which was then stirred at 4° C. for 1 hour.

Then, centrifugation operation was carried out, and the supernatant was discarded. Again, 50% saturated ammonium sulfate and PBS (pH 7.4) were added, and the resultant was slightly stirred and then centrifuged, followed by discarding the supernatant. PBS (pH 7.4) was added to the resultant precipitate for resolution. In addition, buffer exchange to phosphate buffer was performed using a desalting column, PD-10 (from GE Healthcare). From the solution, only an IgG fraction was purified by affinity chromatography using a protein G column (from GE Healthcare). 0.1 M glycine (pH 2.7) was used as an eluting solution, and buffer exchange to PBS (pH 7.4) was performed using the desalting column PD-10. The measurement of absorbance at UV 280 nm revealed that 15 mg of the anti APP-SP monoclonal antibody had been obtained.

(7) ELISA Evaluation of Purified Anti APP-SP Monoclonal Antibody

Figure 3:
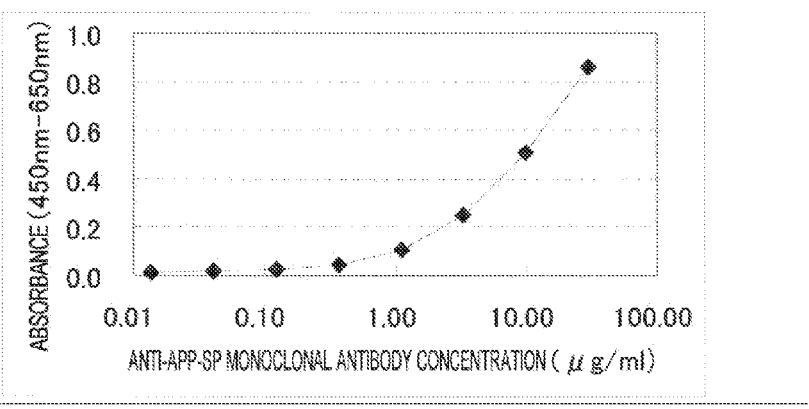
FIG. 3 shows the results of ELISA measurement of an anti APP-SP monoclonal antibody.

The same ELISA as in (3) was carried out using the anti APP-SP monoclonal antibody obtained in (6). However, a solution containing the anti APP-SP monoclonal antibody obtained in (6) was used for a primary antibody. The results are shown in FIG. 3.

Thus, after purification, the reactivity of the antibody against APP-SP could be confirmed.

(8) Evaluation of Specificity of Anti APP-SP Monoclonal Antibody

Figure 4:
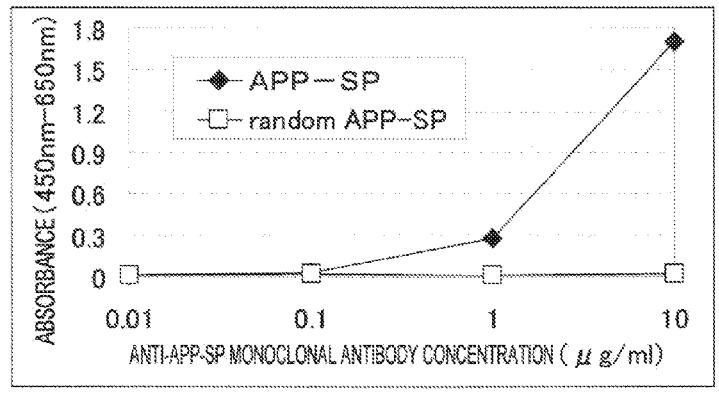
FIG. 4 shows the results of ELISA measurement for random APP-SP (SEQ ID NO: 2).

To evaluate the reaction specificity of the antibody obtained in this Example, its reactivity was evaluated to random APP-SP (SEQ ID NO: 2) prepared by shuffling the amino acid sequence of the antigen APP-SP having exhibited reactivity in (7), by using the same ELISA as in (7). The results are shown in FIG. 4. From these results, the reaction specificity was confirmed to be high since the antibody did not exhibit reactivity to random APP-SP containing the same amino acid components as those of APP-SP but having a different arrangement sequence.

(9) Evaluation of Anti APP-SP Monoclonal Antibody in Dot Blot Method

Figure 5:
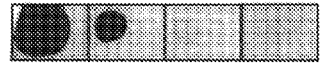
FIG. 5 shows the results of measurement in a dot-blot method.

It was examined whether the antibody obtained in this Example could also detect APP-SP in a dot blot method. 1 µL each of 1% PEG60 aqueous solutions containing 1 mg/mL, 0.1 mg/mL, 0.01 mg/mL, and 0 mg/mL APP-SP were each added dropwise to a nitrocellulose membrane (from GE Healthcare) and dried. The resultant was immersed in a solution containing 1% skim milk, TBS (pH 7.5), and 0.1% Tween20 and shaken for 1 hour. Then, the solution was discarded; a solution containing 0.2% skim milk, TBS (pH 7.5), and 0.1% Tween20, containing 10 µg/mL of the anti APP-SP monoclonal antibody was added; and shaking was performed for 1 hour. Thereafter, the antibody solution was discarded, and washing operation was performed 3 times with the solution containing 0.2% skim milk, TBS (pH 7.5), and 0.1% Tween20 (shaking was carried out for 5 minutes per operation). Then, thereto was added an anti mouse IgG alkaline phosphatase conjugate (from Sigma) diluted 1:4,000 with the solution containing 0.2% skim milk, TBS (pH 7.5), and 0.1% Tween20, followed by shaking for 1 hour. After discarding the solution, washing operation was performed 3 times with the solution containing 0.2% skim milk, TBS (pH 7.5), and 0.1% Tween20 (shaking was carried out for 5 minutes per operation). Finally, NBT/BCIP solution (from PIERCE) was added, followed by shaking for 30 minutes. The results are shown in FIG. 5. From these results, the antibody was shown to be also capable of detecting APP-SP in the dot blot method.

Reference Example (1) Synthesis of Peptide

A peptide in which a Cys residue was added to the N-terminus of the human amyloid precursor protein signal peptide (APP-SP, SEQ ID NO: 1) (hereinafter, sometimes referred to as Cys-APP-SP, SEQ ID NO: 3) was chemically synthesized under commission to GL Biochem Ltd. (Shanghai).

The chemical synthesis of the peptide was performed by Fmoc solid phase synthesis method. The chemically synthesized peptide (Cys-APP-SP) was purified by a concentration gradient method in which an ODS column was used and 0.1% TFA-containing water/MeCN was used as a mobile phase.

(2) Preparation of Antigen by Cross-Linking Reaction between Cys-APP-SP and Keyhole Limpet Hemocyanin (KLH)

A 10 mg/mL DMF solution of Cys-APP-SP and a solution containing 1% PEG60, 83 mM sodium phosphate buffer, 100 mM EDTA, and 0.9 M NaCl (pH 7.2) were mixed at a volume ratio of 1:4. This mixed solution and 10 mg/mL maleimide-activated KLH were mixed in equal amounts and stirred at room temperature for 4 hours. A desalting column was used to separate only a fraction presumed to contain a cross-linking reaction product between the carrier protein and APP-SP.

(3) KLH-Cys-APP-SP Administration to Mouse

The antigen prepared in (2) was immunized into a mouse according to an administration schedule as shown in Table 2, and blood collection was carried out. A serum fraction was obtained from the blood obtained in the blood collection by a centrifugation operation.

An adjuvant was mixed in an amount equal to 0.2 mg/mL of the fraction as an antigen (resulting in a concentration of 0.1 mg/mL), and the resultant was sonicated to make an emulsion to provide an antigen solution. As the adjuvant, Freund's complete adjuvant (from Sigma) was used at priming immunization (the 0th day) and Freund's incomplete adjuvant (from Sigma) was used during booster immunization (on or after 14th day).

TABLE 2

| Number of Days | Work Item |
| --- | --- |
| 0 | Blood Collection 1, Antigen Administration (20 µg) |
| 14 | Antigen Administration (10 µg) |

TABLE 2-continued

| Number of Days | Work Item |
|---|---|
| 22 | Blood Collection 2 |
| 28 | Antigen Administration (10 μg) |
| 35 | Blood Collection 3 |
| 42 | Antigen Administration (10 μg) |
| 49 | Blood Collection 4 |
| 56 | Antigen Administration (10 μg) |
| 63 | Blood Collection 5 |
| 70 | Antigen Administration (10 μg) |
| 77 | Blood Collection 6 |
| 85 | Antigen Administration (10 μg) |
| 91 | Blood Collection 7 |

(4) Measurement of Antibody Titer

To evaluate the results of the immunization performed in (3), the serum obtained by the blood collection method shown in Table 2 was used to carry out ELISA as follows.

A 0.002% Tween20 solution containing 10 μg/mL APP-SP was added in an amount of 100 μL/well to a microwell plate (from Nunc) and placed in a state allowed to stand at room temperature overnight. The following day, the solution in the wells was discarded, and 250 μL of a solution containing 3% BSA, 0.1% $NaN_3$, and PBS (pH 7.4) was added, followed by allowing the resultant to stand at room temperature for 2.5 hours. Subsequently, the solution in the wells was discarded, and 100 μL of a solution was added in which serum was diluted 1:100 with a solution containing 1% BSA, 0.05% $NaN_3$, TBS (pH 7.5) (a primary antibody diluent). After standing for 1 hour, the resultant was washed 6 times with PBST (PBS (pH 7.4), 0.1% Tween20). Then, HRP-labeled Anti mouse IgG (H+L chain) (from MBL) as a secondary antibody was diluted 1:4,000 with 1% BSA-containing PBS (pH 7.4), and 100 μL of the resultant was added. After standing for 1 hour, washing was carried out 6 times with PBST. Then, 100 μL of TBS+ was added thereto, and the resultant was allowed to stand for 30 minutes. 100 μL of 2 N sulfuric acid was added to stop enzyme reaction, and absorbance at 450 nm and 650 nm was measured. The results are shown in FIG. 6. These results showed that an antibody against APP-SP was not obtained.

Advantageous Effects of Invention

According to an aspect of the invention, an antibody against the amyloid precursor protein signal peptide (APP-SP) can be provided. The anti APP-SP antibody according to an aspect of the invention has the possibility of being capable of used for the diagnosis, treatment, or the like of Alzheimer's disease.

INDUSTRIAL APPLICABILITY

According to an aspect of the invention, an antibody against the amyloid precursor protein signal peptide (APP-SP) can be provided. The anti APP-SP antibody according to an aspect of the invention has industrial applicability in that it can be used for the diagnosis, treatment, or the like of Alzheimer's disease.

SEQUENCE LISTING FREE TEXT

SEQ ID NO: 1 shows the amino acid sequence of the amyloid precursor protein signal peptide (APP-SP).
SEQ ID NO: 2 shows the amino acid sequence of random APP-SP prepared by shuffling the amino acid sequence of APP-SP.
SEQ ID NO: 3 shows the amino acid sequence of a peptide in which a Cys residue is added to the N-terminus of APP-SP.

What is claimed is:

1. A hybridoma indicated by receipt number NITE ABP-1198.

```
SEQUENCE LISTING

<160> NUMBER OF SEQ ID NOS: 3

<210> SEQ ID NO 1
<211> LENGTH: 17
<212> TYPE: PRT
<213> ORGANISM: Human

<400> SEQUENCE: 1

Met Leu Pro Gly Leu Ala Leu Leu Leu Leu Ala Ala Trp Thr Ala Arg
1               5                   10                  15

Ala

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct - PRT

<400> SEQUENCE: 2

Leu Gly Ala Ala Ala Pro Ala Ala Arg Thr Leu Leu Met Leu Leu Trp
1               5                   10                  15

Leu

<210> SEQ ID NO 3
```

```
<211> LENGTH: 18
<212> TYPE: PRT
<213> ORGANISM: Artificial Sequence
<220> FEATURE:
<223> OTHER INFORMATION: Synthetic Construct - PRT

<400> SEQUENCE: 3

Cys Met Leu Pro Gly Leu Ala Leu Leu Leu Leu Ala Ala Trp Thr Ala
1               5                   10                  15

Arg Ala
```